US005425719A

United States Patent [19]

Lessing, Jr.

[11] Patent Number: 5,425,719

[45] Date of Patent: Jun. 20, 1995

[54] PERITONEAL DIALYSIS CATHETER BELT PACK

[76] Inventor: Kennith C. Lessing, Jr., 1344 Laverte Cir., Mableton, Ga. 30059

[21] Appl. No.: 67,596

[22] Filed: May 27, 1993

[51] Int. Cl.[6] ............ A61M 25/02

[52] U.S. Cl. ............ 604/179; 224/224; 604/174

[58] Field of Search ............ 604/174, 179; 224/228, 224/224; 3/312, 319; 128/DIG. 26

[56] References Cited

U.S. PATENT DOCUMENTS 2,298,600 10/1942 Stember ............ 224/228
4,139,130 2/1979 Glusker et al. ............ 2/312
4,411,267 10/1983 Heymann ............ 224/224
4,523,703 6/1985 McKenna ............ 224/228
4,569,348 2/1986 Hasslinger ............ 604/179
4,596,560 6/1986 Simpson ............ 604/174
4,666,432 5/1987 McNeish et al. ............ 604/179
4,799,923 1/1989 Campbell ............ 604/179
4,955,867 9/1990 Endo ............ 604/179
5,048,512 9/1991 Turner et al. ............ 604/179
5,209,385 5/1993 Ledesma ............ 224/228

*Primary Examiner*—Paul J. Hirsch

[57] ABSTRACT

A belt-pack for containing and securing surgically implanted catheters embodying a pouch means and a belt means with two end portions, one end portion permanently attached to the pouch means and one end portion thereof extending around the waist of a patient and overlapping and detachably connected to the pouch means.

3 Claims, 7 Drawing Sheets

1

6

4

7

5

PERITONEAL DIALYSIS CATHETER BELT PACK

BACKGROUND OF THE INVENTION

1. Field of the Invention

This invention relates in general to a belt pack for containing and securing surgically-implanted catheters. More specifically, the present invention relates to catheters surgically implanted for the purpose of Contiuous Ambulatory and Continuous Cycling Peritoneal Dialysis.

2. Prior Art

More than 80,000 Americans have chronic kidney failure and have to find other ways of doing the job their kidneys can no longer perform. Two such ways are Continuous Ambulatory and Continuous Cycling Peritoneal Dialysis which use the lining of the abdomen as a natural filter to remove water and wastes from the blood by putting a sterile cleansing solution, called dialysate, into the abdominal cavity and then draining this fluid after it has absorbed water wastes. There are two ways to fill and drain the peritoneal cavity:

(1) manually, by Continuous Ambulatory Peritoneal Dialysis, 4–6 times every day, or (2) automatically, by Continuous Cycling Peritoneal Dialysis, overnight while the patient sleeps.

Both procedures require the surgical implantation of a catheter apparatus which creates the problem of containing and securing the catheter apparatus when not being used in either treatment procedure. Current containment devices consist of securing the catheter apparatus by merely taping a section of the catheter apparatus directly to the patient's body. This taping method is unsatisfactory because:

(1) Frequent removal of the tape, as in the Continuous Ambulatory Peritoneal Dialysis treatment method, 4–6 times daily, can result in physical discomfort.

(2) The tape is not re-usable.

(3) The tape secures only a portion of the catheter apparatus, leaving the majority of the apparatus exposed.

(4) The taping method is aesthetically undesirable because it inhibits the pursuit of a normal, active lifestyle, including physical intimacy.

SUMMARY OF THE INVENTION

The principle object of the present invention is to provide a more convenient, comfortable and aesthetically desirable device for use in securing surgically-implanted peritoneal dialysis catheters by containment in a durable, re-usable belt pack.

BRIEF DESCRIPTION OF THE DRAWINGS

A containment device embodying features of my invention is illustrated in the accompanying drawings, forming part of this application, in which.

DETAILED DESCRIPTION

Figure 1:
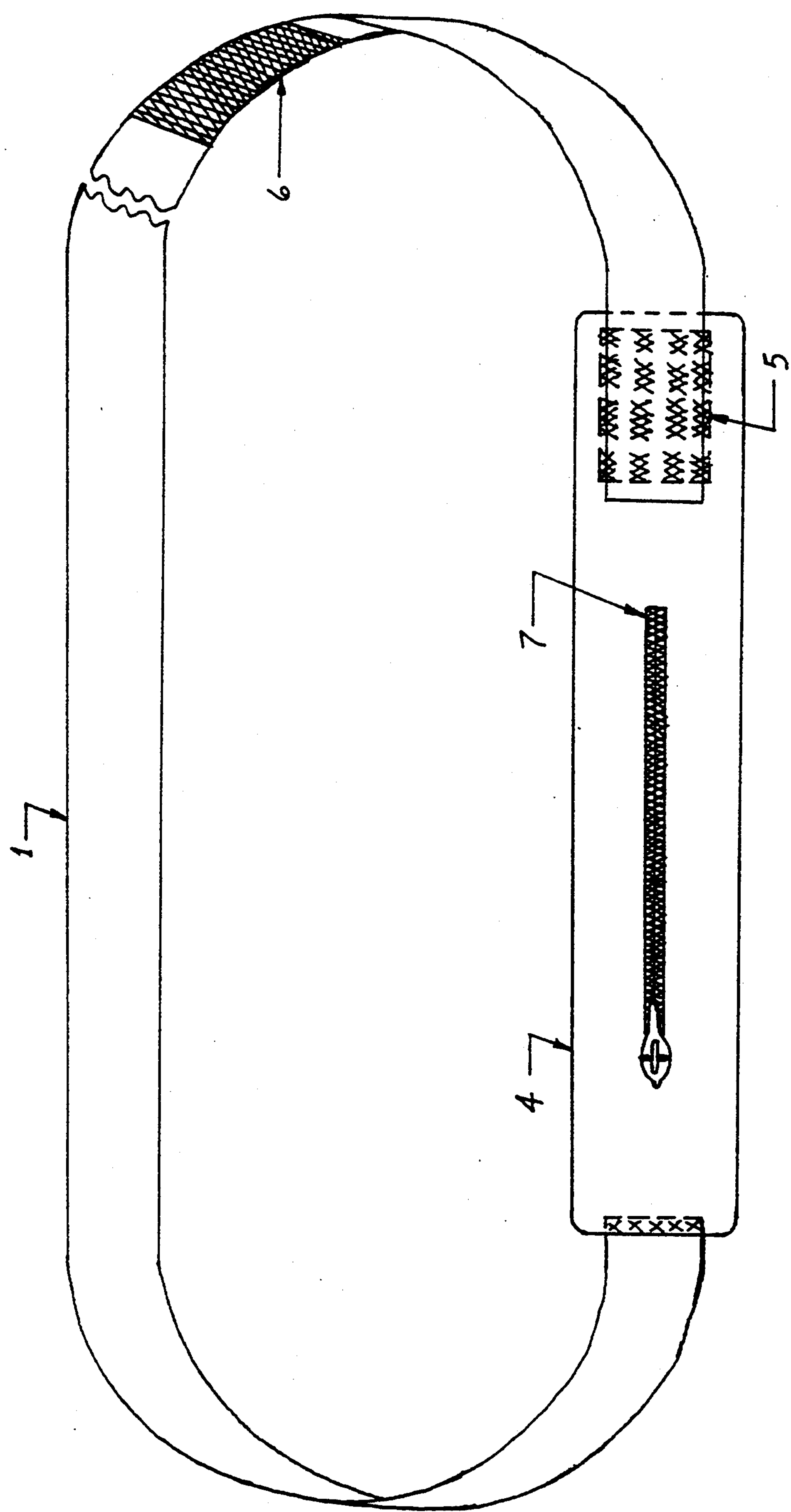
FIG. 1 is an illustration of a peritoneal dialysis catheter belt pack and the majority of component parts.

Referring now to the drawings for a better understanding of my invention, I show a belt-like member 1 preferably of flexible woven material with two end portions 2 & 3 joined to a pouch-like member 4 preferably of stable, woven material; one end portion 2 being permanently attached and one end portion 3 releasingly fastened to the pouch-like member 4. The belt-like member 1 is of a length to extend around the waist of a patient having a surgically-implanted catheter apparatus and overlap an adjacent portion of the pouch-like member 4 as shown in FIG. 1.

Figure 4:
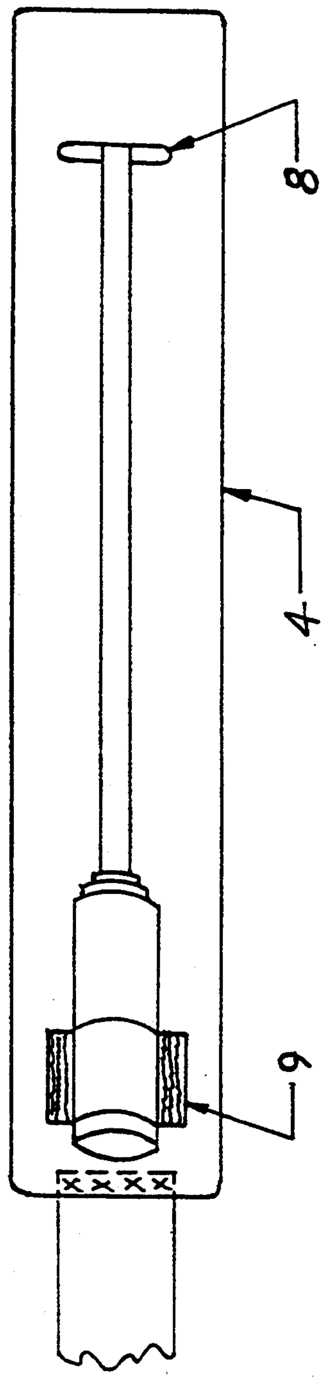
FIG. 4 is an illustration of the catheter apparatus inserted and secured to the inside-facing back piece of the pouch-like member.
Figure 5:
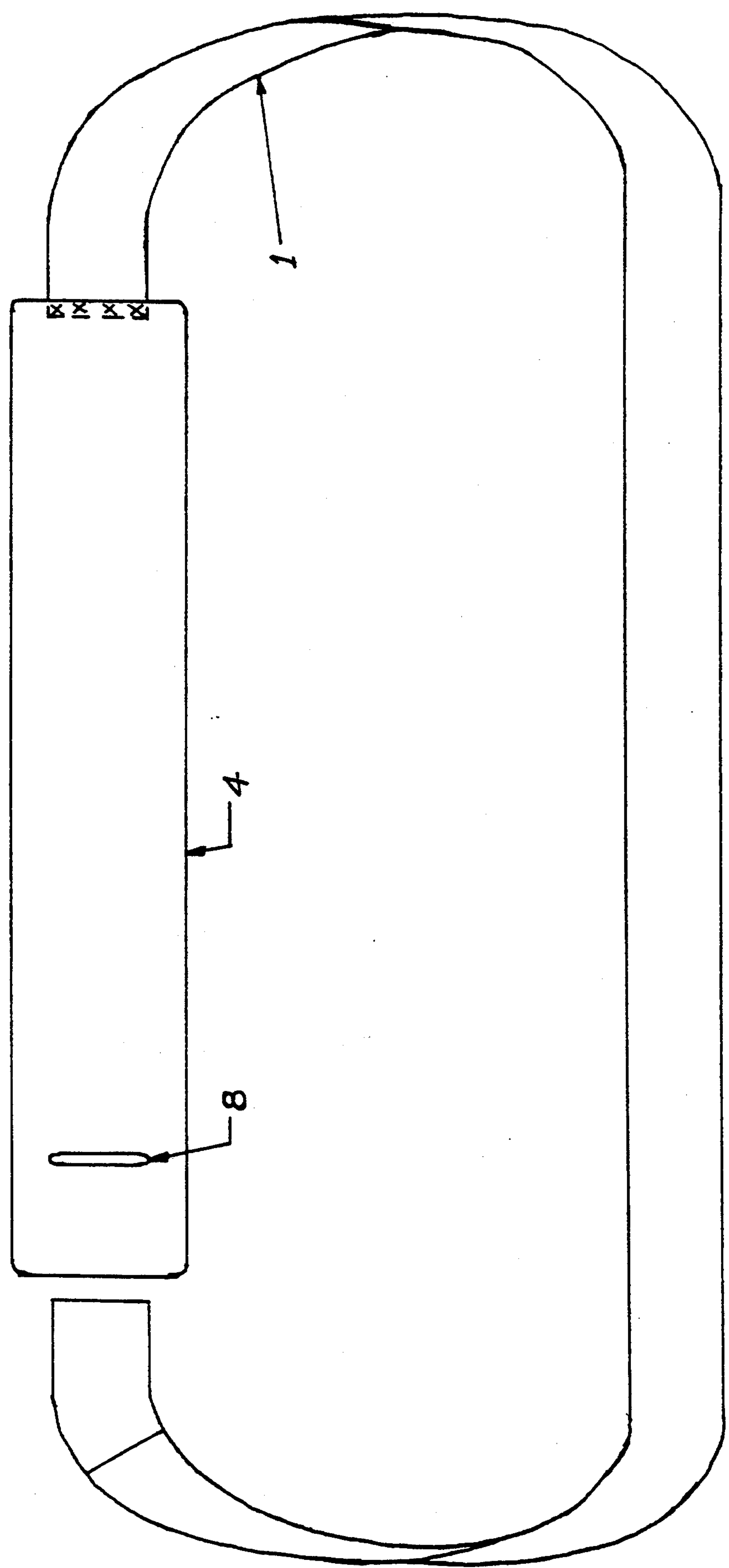
FIG. 5 is an illustration of the outside-facing back piece of the pouch-like member.
Figure 6:
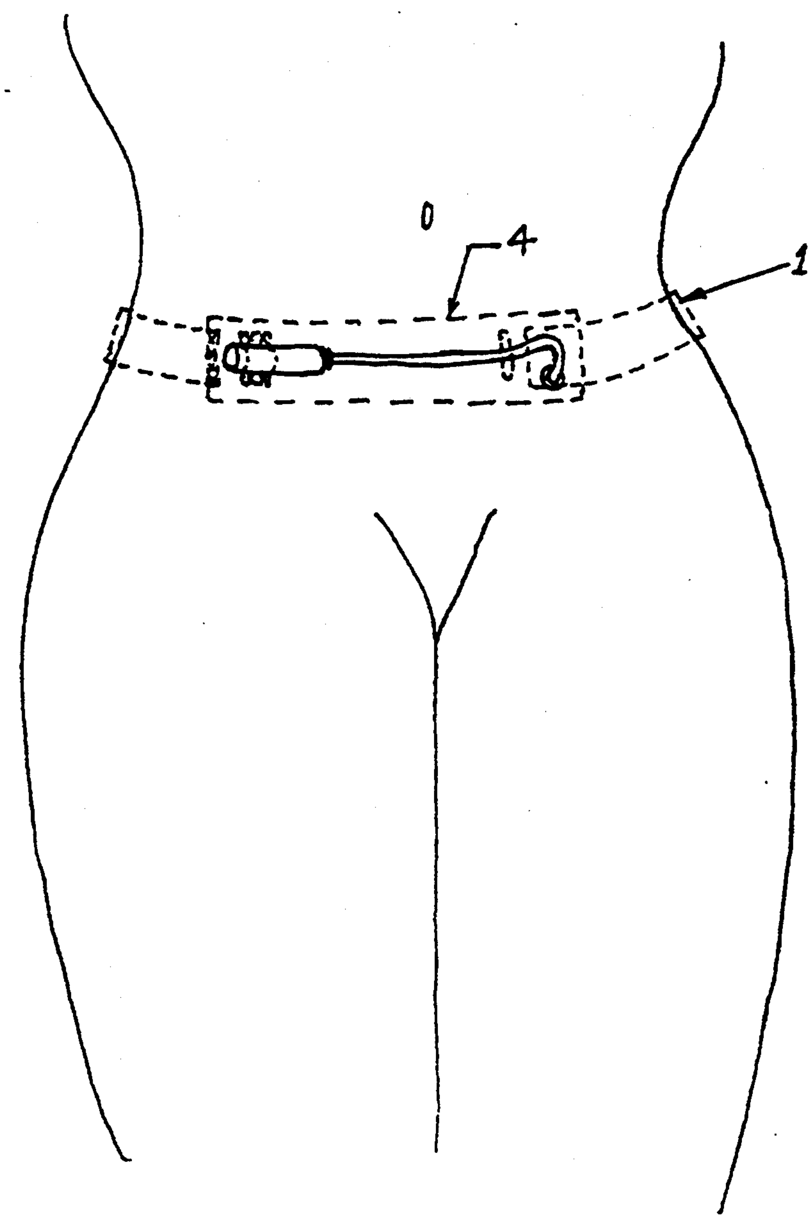
FIG. 6 is an illustration of a surgically-implanted catheter apparatus without a peritoneal dialysis catheter belt pack.

The releasable end portion 3 of the belt-like member 1 and the fastening end of the pouch-like member 4 have cooperating surfaces facing each other, with one surface carrying a plurality of small, hook-like members 5 in position to engage a felt-like material 6 carried by the facing surface of the releasable end portion 3 of the belt-like member 1. The pouch-like member 4 is composed of two pieces, a front and back, preferably of stabe, woven material of a size sufficient to enclose and contain the catheter apparatus. The front piece FIG. 2 contains the reclosable opening 7 running lengthwise (horizontally) across the center to facilitate access to the catheter apparatus with a section of small hook-like members 5 attached to the fastening end to engage the section of felt-like material 6 attached to the fastening end of the belt-like member 1. The back piece FIG. 3 & FIG. 5 contains a vertical, buttonhole-like slit 8 on one end through which the catheter apparatus is inserted with a beltloop-like member 9 preferably of flexible, woven material attached to the inside-facing opposite end to secure the catheter apparatus. FIG. 4 shows the inside-facing back piece with catheter apparatus inserted and secured. The pouch-like member 4 is formed by placing the front FIG. 2 and back FIG. 3 pieces together and securing all open edges. The permanently-attached end portion 2 of the belt-like member 1 is centrally positioned and secured. The section of small, hook-like members 5 is attached to the fastening end of the pouch-like member 4, ready to engage the felt-like material 6 attached to the belt-like member 1. The Peritoneal Dialysis Belt Pack is now ready for the patient's use.

From the foregoing description the operation of my Peritoneal Dialysis Catheter Belt Pack will be readily understood.

Figure 2:
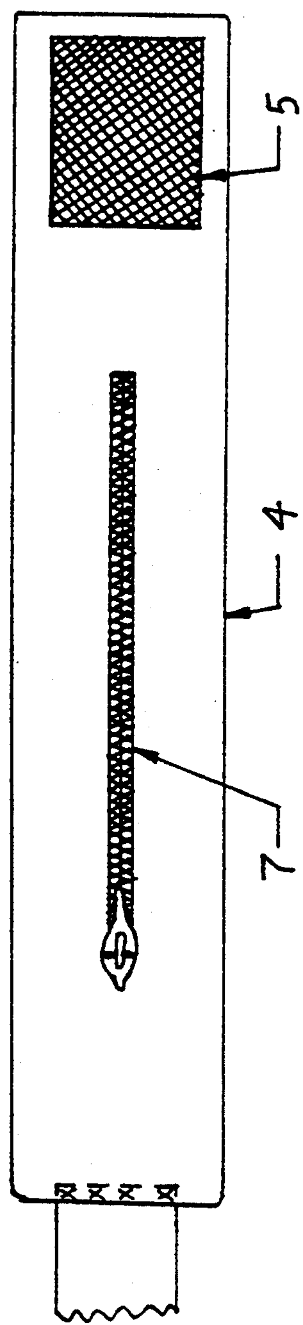
FIG. 2 is an illustration of the front piece of the pouch-like member.
Figure 3:
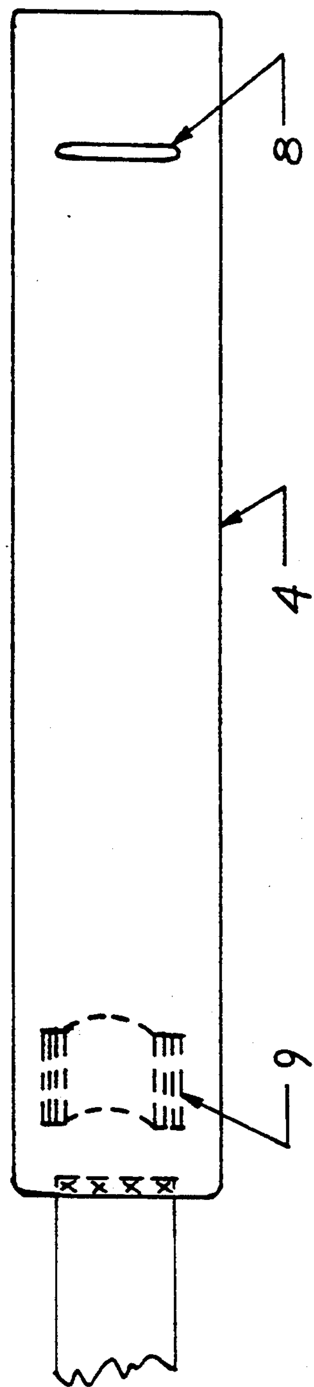
FIG. 3 is an illustration of the inside-facing view of the back piece of the pouch-like member.
Figure 7:
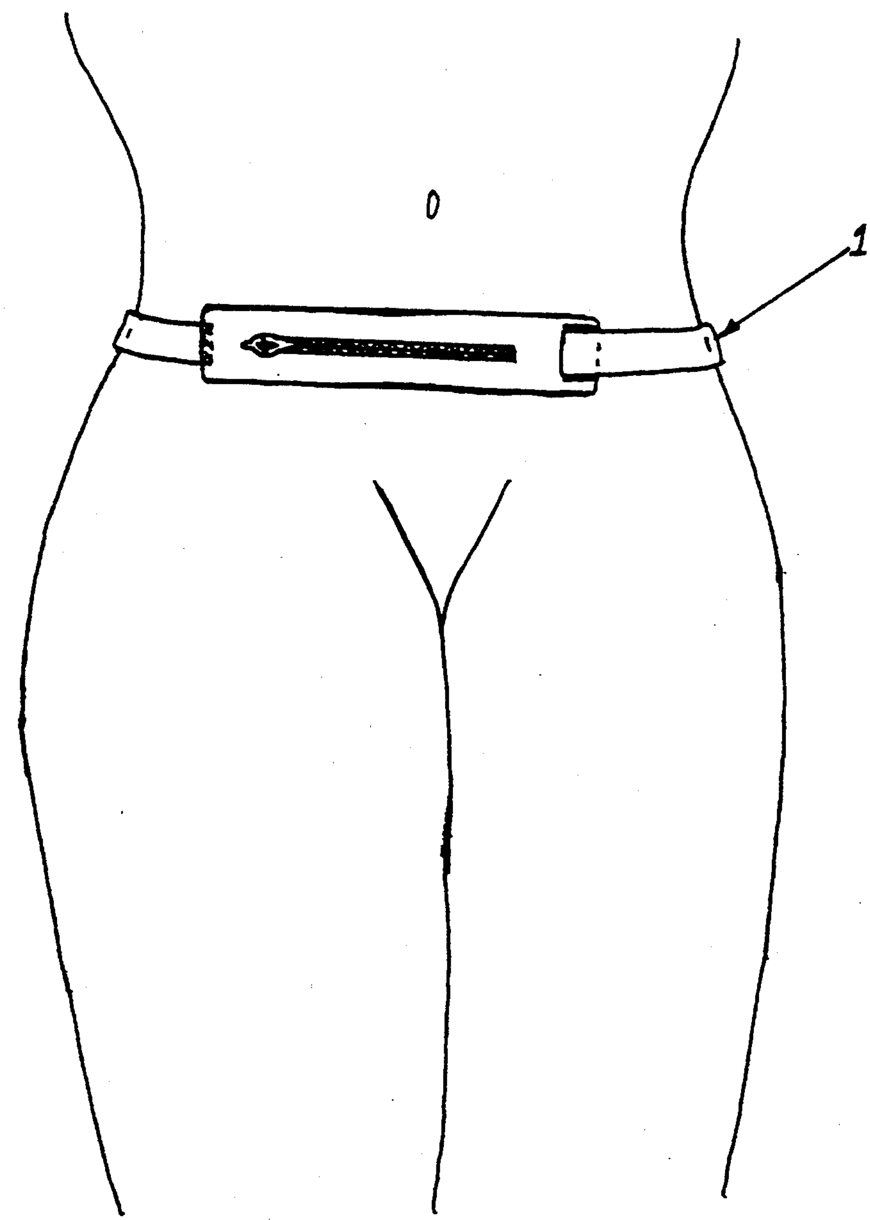
FIG. 7 is an illustration of a surgically-implanted catheter apparatus contained and secured within a peritoneal dialysis catheter belt pack.

The catheter apparatus is inserted through the buttonhole-like slit 8 in the back piece FIG. 3 of the pouch-like member 4 and secured by placing its end through the beltloop-like member 9 which is accessed through the re-closable opening 7 in the front piece FIG. 2 of the pouch-like member 4. With the re-closable opening 7 remaining open, the patient wraps the belt-like member 1 around his waist in position for the hook-like members 5 to engage the felt-like material 6. Next, the patient adjusts the catheter apparatus within the pouch-like member 4 and closes the re-closable opening 7. The patient is now ready to pursue his regular activities with the catheter apparatus fully contained and securely held in place as shown in FIG. 7.

The hook-like members and felt-like material are conventional materials such as nylon or polyolefins.

The belt-like member is made of conventional belt-type material such as non-roll waistband elastic, nylon webbing or other synthetic or natural flexible woven materials.

The pouch-like member is made of conventional stable woven materials such as cotton, polyester, cotton-polyester blends or other synthetic or natural stable woven materials.

Furthermore, the materials might be conventional lingerie and undergarment materials so that the peritoneal dialysis catheter belt pack also functions as a conventional undergarment The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claim appended hereto.

I claim:

1. A peritoneal dialysis catheter apparatus containment device comprising:

a belt having two ends, one end comprising an integral pouch, said pouch having a front opening, a back opening, and a first releasable attaching means adjacent to said front opening, said front opening includes a zipper for selectively opening and closing said pouch, the other end of said belt extending from said pouch and having a second means for releasably attaching said other end to said one end, said first and second releasable attaching means being hook and felt-like fasteners.

2. The peritoneal dialysis catheter apparatus containment device as claimed in claim 1, further comprising a belt-like loop means for securing catheter apparatus to the rear of said pouch.

3. The peritoneal dialysis catheter apparatus containment device as claimed in claim 1 whereby said back opening is for threading a catheter apparatus therethrough.

* * * * *